US010758376B2

(12) United States Patent
Kaltenborn et al.

(10) Patent No.: US 10,758,376 B2
(45) Date of Patent: Sep. 1, 2020

(54) FOOT PROSTHESIS

(71) Applicant: OTTO BOCK HEALTHCARE GMBH, Duderstadt (DE)

(72) Inventors: Sven Kaltenborn, Duderstadt (DE); Georg Gehrmann, Gottingen (DE); Miclas Schwartz, Gottingen (DE)

(73) Assignee: OTTOBOCK SE & CO. KGAA, Duderstadt (DE)

( * ) Notice: Subject to any disclaimer, the term of this patent is extended or adjusted under 35 U.S.C. 154(b) by 0 days.

(21) Appl. No.: 15/570,232

(22) PCT Filed: Apr. 27, 2016

(86) PCT No.: PCT/EP2016/059415
§ 371 (c)(1),
(2) Date: Oct. 27, 2017

(87) PCT Pub. No.: WO2016/174096
PCT Pub. Date: Nov. 3, 2016

(65) Prior Publication Data
US 2018/0125679 A1 May 10, 2018

(30) Foreign Application Priority Data
Apr. 29, 2015 (DE) .................... 10 2015 207 936

(51) Int. Cl.
*A61F 2/66* (2006.01)
*A61F 2/74* (2006.01)
(Continued)

(52) U.S. Cl.
CPC .............. *A61F 2/66* (2013.01); *A61B 5/1038* (2013.01); *A61B 5/112* (2013.01); *A61F 2/6607* (2013.01);
(Continued)

(58) Field of Classification Search
None
See application file for complete search history.

(56) References Cited

U.S. PATENT DOCUMENTS 8,709,091 B2    4/2014   Rhodes et al.
8,986,398 B2    3/2015   Poulson, III et al.
(Continued)

FOREIGN PATENT DOCUMENTS

| EP | 1974699 A1 | 10/2008 |
| WO | 2014039885 A1 | 3/2014 |
| WO | 2014057086 A1 | 4/2014 |

OTHER PUBLICATIONS

PCT International Search Report for PCT International Patent Application No. PCT/EP2016/059415, dated Aug. 9, 2016.

*Primary Examiner* — David H Willse
(74) *Attorney, Agent, or Firm* — Holland & Hart, LLP

(57) ABSTRACT

A foot prosthesis having a lower-leg connection part, a foot part, a connecting element with a joint function which connects the lower-leg connection part to the foot part, and a release device, which controls movement of the foot part in relation to the lower-leg connection part. The release device includes an inhibiting device that is designed in such a way that a dorsal extension motion of the foot part in relation to the lower-leg connection part in an angular range from a maximal plantar flexion position to a zero position is inhibited less intensely than a dorsal extension motion of the foot part from the zero position.

28 Claims, 10 Drawing Sheets

(51) Int. Cl.
  *A61B 5/103*    (2006.01)
  *A61B 5/11*     (2006.01)
  *A61F 2/76*     (2006.01)
  *A61F 2/68*     (2006.01)
  *A61F 2/50*     (2006.01)
  *A61F 2/60*     (2006.01)

(52) U.S. Cl.
  CPC .............. *A61F 2/76* (2013.01); *A61F 2/5044* (2013.01); *A61F 2002/503* (2013.01); *A61F 2002/5003* (2013.01); *A61F 2002/5006* (2013.01); *A61F 2002/607* (2013.01); *A61F 2002/6657* (2013.01); *A61F 2002/6818* (2013.01); *A61F 2002/6845* (2013.01); *A61F 2002/6854* (2013.01); *A61F 2002/74* (2013.01); *A61F 2002/745* (2013.01); *A61F 2002/748* (2013.01)

(56) References Cited

U.S. PATENT DOCUMENTS

| | | |
|---|---|---|
| 2008/0255670 A1 | 10/2008 | Boiten et al. |
| 2008/0300692 A1* | 12/2008 | Moser .................. A61F 2/6607 623/55 |
| 2009/0319055 A1* | 12/2009 | Iversen ................ A61F 2/6607 623/49 |
| 2013/0173022 A1 | 7/2013 | Arabian et al. |
| 2014/0074255 A1 | 3/2014 | Starker et al. |
| 2014/0330393 A1 | 11/2014 | Ward et al. |
| 2015/0066153 A1 | 3/2015 | Palmer, III et al. |
| 2017/0056209 A1* | 3/2017 | Mooney ................ A61F 2/6607 |

\* cited by examiner

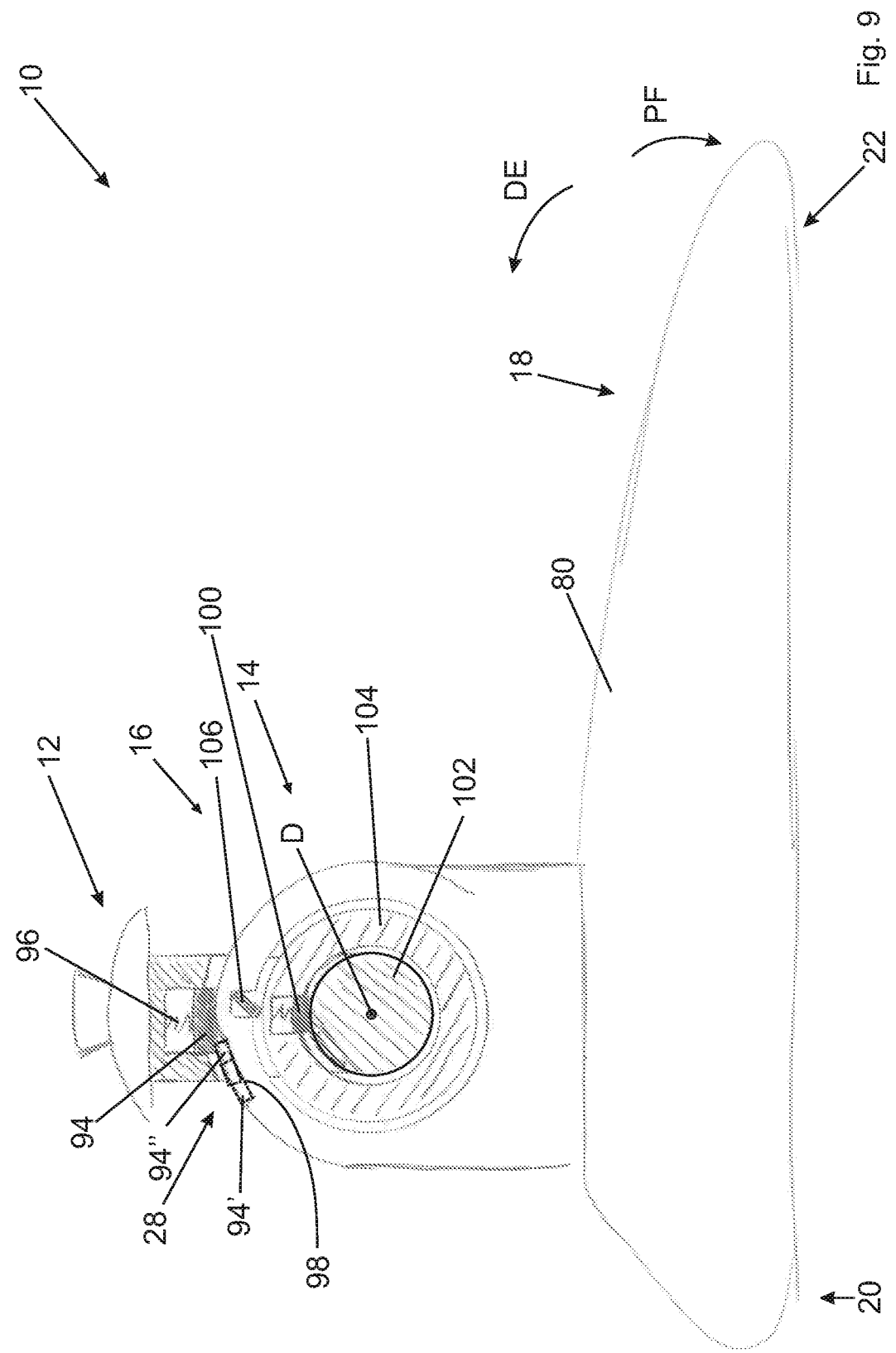

FOOT PROSTHESIS

TECHNICAL FIELD

The invention relates to a foot prosthesis, comprising a lower-leg connection part, a foot part, a connecting element with a joint function which connects the lower-leg connection part to the foot part, and a release device, by means of which a movement of the foot part in relation to the lower-leg connection part can be inhibited and disinhibited.

BACKGROUND

This type of prosthesis is known from U.S. Pat. No. 8,709,091 B2, which has a microprocessor that uses sensor data to record when the gait cycle has reached the stage at which the joint must be released. The disadvantage of this type of prosthesis is the high level of complexity involved in its production and maintenance.

WO 2014/039885 A1 describes a prosthesis which also records the gait cycle by means of a microprocessor and a number of sensors. It is possible to store threshold values in a control unit of the prosthesis, which are used to control the actuators of the prosthesis. This type of system is also complex to produce and maintain.

US 2014/0074255 A1 describes an artificial foot that uses a rollable element to seal a fluid channel at exactly the point at which the patient is standing. This prohibits a dorsal extension motion of the foot when the centre of gravity is above the foot. The disadvantage of this type of foot is the increased risk of tripping.

US 2014/0330393 A1 describes a foot with two springs that are used to apply a first torque to a dorsal extension motion up to a zero position and then to apply a second torque. The disadvantage of this type of system is the noise emission.

An additional disadvantage of known prostheses is that it is comparatively complex to adapt the prosthesis if shoes with different heel heights are worn.

SUMMARY

The invention aims to reduce disadvantages of the prior art.

The invention solves the problem by means of a foot prosthesis whose release device has a passive inhibiting device which is designed in such a way that a dorsal extension motion of the foot part in relation to the lower-leg connection part in an angular range from a maximal plantar flexion position to a zero position is inhibited less intensely than a dorsal extension motion of the foot part from the zero position. The inhibiting device is preferably designed such that the zero position is adjustable. The maximal plantar flexion position is the position in which the plantar flexion of the foot part is at its maximum.

The advantage of this type of foot prosthesis is that its structure is particularly simple. This renders a control unit and sensors such as actuators dispensable. The advantage of a hydraulic inhibiting device is that it operates especially quietly when compared with, for example, mechanical inhibiting devices.

Due to the fact that the dorsal extension motion between the maximal plantar flexion position and the zero position is less intensely inhibited than beyond the zero position, the foot part can initially swivel relative to the lower-leg connection part without having to exert too great a resistance after the heel has landed. Conversely, as soon as the centre of gravity of the patient wearing the foot prosthesis is above the foot prosthesis, a further dorsal extension motion is inhibited more intensely or indeed completely prevented. This means that the patient's body does not lose any height.

If the centre of gravity of the patient's body has moved to above the ball of the foot prosthesis, the ankle torque exceeds a release threshold value and, according to a preferred embodiment of the prosthesis, the inhibiting device releases the dorsal extension motion of the foot part. During the subsequent raising of the foot prosthesis, there is thus a greater distance between the ground and the tip of the foot prosthesis, thereby reducing the risk of tripping. If at the beginning of the next gait cycle the foot prosthesis lands on the ground, the foot part executes a plantar flexion motion and the sequence described above is repeated.

Within the scope of the present description, the lower-leg connection part is to be understood particularly to mean a device that is designed to create a direct or indirect mechanical connection to an artificial or natural lower leg. It is therefore possible but not necessary to have an artificial lower leg and/or an artificial knee joint that is connected to the lower-leg connection part such that it can or cannot be detached.

The foot part should be understood particularly to mean the part of the prosthesis that assumes the function of the human foot. In particular, the foot part may comprise a foot shell which lends the prosthesis the appearance of a natural foot. However, this type of foot shell is dispensable.

The connecting element is understood particularly to mean a connection between the lower-leg connection part and the foot part that allows a relative motion of both components, this motion corresponding to the movement of a natural foot. The connecting element may have a swivel joint or be formed by a swivel joint with a fixed rotational axis. This position of the rotational axis may be independent of the angle of rotation of the swivel joint.

However, it is also possible for the connecting element to have several partial joints and a momentary rotational axis, meaning that the rotational axis, by means of which the momentary rotation of the foot part in relation to the lower-leg connection part can be described, changes over time and/or with the progress of motion in the gait cycle. It is also possible that the connecting element is at least partially configured as a flexure bearing. Most prostheses aim to imitate the natural motion sequence as effectively as possible. As the human foot has several partial joints, many prostheses comprise a connecting element with a rotational axis that changes its position over time. The invention relates to prostheses with this type of connecting element.

The dorsal extension motion of the foot part from the zero position should be understood to mean a swivelling motion of the foot part that occurs beyond the zero position in the dorsal extension direction.

The connecting element preferably connects the lower-leg connection part with the foot part in the same way that an ankle joint does. This is to be understood particularly to mean that the connecting element emulates the movement of a human ankle joint. The connecting element may thus refer to a swivel joint; however, this is not essential.

The connecting element is preferably configured such that it exhibits a less intense resistance to a dorsal and/or plantar motion, for example by a factor of at least five, than to a medial or lateral motion.

The foot part can preferably be pivoted in relation to the lower-leg connection part. This should be understood particularly to mean that the release device impedes a movement between the foot part and lower-leg connection part so little that the foot part executes or can execute a dorsal extension motion in the normal gait cycle. The release device is preferably configured such that it exhibits an at least three times greater resistance to a dorsal extension motion of the foot part relative to the lower-leg connection part beyond the zero position than between the maximal plantar flexion position and the zero position.

The feature that the inhibiting device is a passive inhibiting device is to be understood particularly to mean that the switching occurs without an actuator. An actuator is a component that can be controlled externally to move another component by applying energy. In particular, the inhibiting device has no actuator and/or energy storage system. The inhibiting device is preferably constructed in such a way that the energy that is required for the transition from a release position, in which the dorsal extension motion is less intensely inhibited, into an inhibiting position, in which the dorsal extension motion is more intensely inhibited, is mechanical, in particular hydraulic energy. In particular, the release device is a passive hydraulic release device.

The zero position should be understood particularly to mean the position of the foot part in relation to the lower-leg connection part at which the transition occurs from a less intensely inhibited swivel capability in the dorsal extension direction to a more intensely inhibited, especially prevented, swivel capability in the dorsal extension direction. It should be noted that it is possible, but not necessary, that the maximal plantar flexion position is reached in the gait cycle. However, the zero position is preferably selected such that a position of the foot part between the zero position and the maximal plantar flexion position is reached in the gait cycle and/or that the foot part is in the zero position when the patient is standing.

In other words, two angular ranges can be determined: the angle between the maximal plantar flexion position and the zero position, and the angle from the zero position to a maximal dorsal extension position. In the former angular range, a dorsal extension motion is easy to achieve, whereas it is considerably more difficult or impossible in the latter angular range.

The feature that the hydraulic cylinder is connected to the foot part and the lower-leg connection part is to be understood particularly to mean that a movable part of the hydraulic cylinder, i.e. the housing or the piston rod, is connected to the foot part and the respective other movable part is connected to the lower-leg connection part.

According to a preferred embodiment, the release device is configured in such a way that it only releases the dorsal extension motion of the foot part beyond the zero position when an ankle torque acting on the foot part lies above a predetermined release threshold value. This has the advantage that it results in a dorsal extension motion of the foot part in relation to the lower-leg connection part beyond the zero position at the end of the standing phase in the gait cycle, as described above, which reduces a distance between the tip of the foot and the ground in the subsequent swing phase, thereby minimising the risk of tripping.

It is possible, but not essential, for the torque threshold value to be known as a torque, i.e. in a unit of the torque. In particular, it is possible that the torque threshold value can be changed to greater and/or smaller torque threshold values without the absolute value of the torque being known. The size of the respective torque threshold value in Newton metres may also be known; however, this is not necessary.

The torque threshold value can be particularly determined by exerting a vertically acting force on the lower-leg connection part, then tilting the lower-leg connection part according to the progression of inclination in the gait cycle and recording the point at which the prosthesis transfers the force into the ground. The projection of the vector product (cross product) of the force and the lever at the point at which the release device switches out of the locking position into the release position on the rotational axis corresponds to the torque threshold value, which is positive.

The release device may be arranged parallel or serially to another spring element of the prosthesis. For example, the spring element is part of the foot part. The spring element preferably comprises a carbon spring. A parallel arrangement should be understood to mean that the mechanical resistances of the release device and the spring element add up. A serial arrangement should be understood to mean that the spring deflection of the release device and the spring element add up.

The release device may be arranged such that it is pressurised or subject to tensile stress. If the release device is pressurised, it is compressed at the end of the standing phase. If the release device is subject to tensile stress, it is decompressed at the end of the standing phase.

According to a preferred embodiment, the prosthesis comprises a pre-loaded spring that is arranged such that it is ready for release upon the heel impact.

According to a preferred embodiment, the inhibiting device is a hydraulic inhibiting device. This means in particular that the inhibiting effect of the inhibiting device is at least also, especially exclusively, effected by hydraulic components.

The release device preferably has a hydraulic cylinder that is connected to the foot part and the lower-leg connection part, and the inhibiting device is connected to the hydraulic cylinder such that a dorsal extension motion of the foot part relative to the lower-leg connection part in an angular range from a maximal plantar flexion position, in which the plantar flexion of the foot part is at its maximum, is less intensely inhibited than a dorsal extension motion of the foot part from the zero position. This type of foot prosthesis is quiet and easy to maintain.

Particularly pertinent to the invention is a foot prosthesis with (a) a lower-leg connection part, (b) a foot part, (c) a connecting element with a joint function that connects the lower-leg connection part with the foot part, and (d) a release device, by means of which a movement of the foot part in relation to the lower-leg connection part can be inhibited and disinhibited, wherein (e) the release device has a passive hydraulic inhibiting device which is designed in such a way that a dorsal extension motion of the foot part in relation to the lower-leg connection part in an angular range from a maximal plantar flexion position, in which the plantar flexion of the foot part is at its maximum, to a zero position is inhibited less intensely than a dorsal extension motion of the foot part from the zero position, wherein this foot prosthesis preferably comprises the release device described in the previous section. The preferred embodiments presented in the present description refer to this invention.

The inhibiting device preferably has a first fluid line through which the hydraulic fluid flows when the foot part executes a dorsal extension motion beyond the zero position, wherein the first fluid line has a first flow resistance, wherein the inhibiting device also comprises a bypass line via which the hydraulic fluid flows when the foot part executes a dorsal extension motion between the maximal plantar flexion and the zero position, wherein the bypass line has a bypass flow resistance that is smaller than the first flow resistance. This should be understood particularly to mean that the bypass flow resistance is a maximum of one third, especially a maximum of one fifth, of the first flow resistance. This renders a dorsal motion between the maximal plantar flexion position and the zero position considerably easier than a dorsal extension motion beyond the zero position.

This causes, as described above, the weight to simply be transferred to the prosthetic foot once the prosthetic foot has landed. As soon as the weight has been fully transferred to the prosthetic foot, the ankle torque—according to a preferred embodiment—must exceed the release threshold value so that another dorsal extension movement occurs. This results in a natural motion sequence with a low risk of tripping.

Within the scope of the present description, the flow resistance is to be understood to mean the quotient of pressure and flow rate, for example when the flow rate is 1 millilitre per second.

The bypass line is preferably connected to the hydraulic cylinder in such a way that a tapping point of a tap opening along a longitudinal axis of the hydraulic cylinder can be adjusted in order to adjust the zero position. The tap opening is the opening from which the hydraulic fluid can move out of the hydraulic cylinder and into the bypass line. As soon as the piston of the hydraulic cylinder has passed the tapping point, the inhibiting device inhibits or prevents a further movement of the piston, especially until the ankle torque has exceeded the release threshold value.

According to a preferred embodiment, the first fluid line has a check valve that is configured to prevent a dorsal extension motion of the foot part beyond the zero position, provided that the maximum ankle torque is not above the release threshold value, and to release the dorsal extension motion beyond the zero position if the ankle torque is above the release threshold value. This type of check valve is robust, durable and quiet, as well as easy to produce. A check valve is to be understood to mean a component that allows a flow of the hydraulic fluid in only one flow direction. For example, the check valve refers to a return valve or a sequence valve.

It is beneficial if the inhibiting device has a second fluid line through which the hydraulic fluid flows if the foot part executes a plantar flexion motion, wherein the second fluid line has a second flow resistance that is smaller than the first flow resistance. This should be understood particularly to mean that the second flow resistance is a maximum of one third, especially a maximum of one fifth, of the first flow resistance of the first fluid line. This renders a plantar flexion motion, as it is executed by the foot part at the beginning of the gait cycle by placing the heel on the ground, comparatively easy. This results in a gait that is comparable with a natural gait.

According to a preferred embodiment, the release device has a second hydraulic cylinder that is connected to the inhibiting device such that a dorsal extension motion of the foot part beyond the zero position causes hydraulic fluid to flow out of the second hydraulic cylinder, through the first fluid line and into the first hydraulic cylinder; a dorsal extension motion between the maximal plantar flexion position and the zero position causes the hydraulic fluid to flow through the bypass line; and a plantar flexion motion causes the hydraulic fluid to flow out of the first hydraulic cylinder, through the second fluid line and into the second hydraulic cylinder.

It should be noted that the first fluid line, the second fluid line and/or the bypass line may comprise mutual line sections.

Alternatively, the hydraulic cylinder is configured to be dual-acting and connected to the inhibiting device in such a way that a dorsal extension motion of the foot part beyond the zero position causes the hydraulic fluid to flow out of an outlet opening, which is arranged at an outlet end of the hydraulic cylinder, through a first fluid line and, if relevant, through an inlet opening, which is arranged at an inlet end that lies opposite to the outlet end, and back into the hydraulic cylinder; a dorsal extension motion between the maximal plantar flexion motion and the zero position causes the hydraulic fluid to flow through the tap opening and the bypass line; and a plantar flexion movement causes the hydraulic fluid to flow through the second fluid line. It is indeed conceivable and in line with the invention that, alongside a dual-action hydraulic cylinder, a second hydraulic cylinder is available; however, this causes an increase in production complexity, which in most cases is undesirable.

According to a preferred embodiment; the release device has a friction brake and a mechanical return element, wherein the friction brake and the return element are arranged in such a way that a dorsal extension motion of the foot part is subject to more intense braking than a plantar flexion motion. For example, the friction brake is pre-loaded on an inhibiting structure by means of a spring.

It is beneficial if the inhibiting device comprises a pin, which is rigidly connected to the foot part; an outer rim, which is rigidly connected to the lower-leg connection part; and an intermediate ring, which is arranged so as to be rotatable relative to the pin and relative to the outer rim, wherein the mechanical return element is arranged such that the intermediate ring only moves upon a dorsal extension motion of the foot part in relation to the pin or in relation to the lower-leg connection part. The result of this is that the friction brake, which—according to a preferred embodiment—exerts a frictional force between the intermediate ring and either the lower-leg connection part or the foot part, only exerts this frictional force if the foot part conducts a dorsal extension motion.

BRIEF DESCRIPTION OF THE DRAWINGS

In the following, the invention will be explained in more detail by way of the attached drawings. They show FIG. 1 a foot prosthesis according to the invention in a dorsally extended position at the end of the swing phase of a gait cycle, FIG. 2a a schematic of the release device of the foot prosthesis according to FIG. 1, FIG. 2b a detailed view of the second hydraulic cylinder, FIG. 3 a schematic depiction of the gait cycle for the purpose of clarifying how the foot prosthesis according to the invention operates, FIG. 4 the foot prosthesis in its zero position, which may also be referred to as the neutral position, FIG. 5 the foot prosthesis in the zero position when it is being used in a shoe with a greater heel height, FIG. 6 the foot prosthesis in its zero position when it is being used in a shoe with a lower heel height, FIG. 7 a perspective view of a foot prosthesis according to a second embodiment of the invention and FIG. 8 a schematic of a release device for a foot prosthesis according to a second embodiment of the invention.

FIG. 9 shows a foot prosthesis according to the invention according to a second embodiment of the invention.

DETAILED DESCRIPTION

Figure 1:
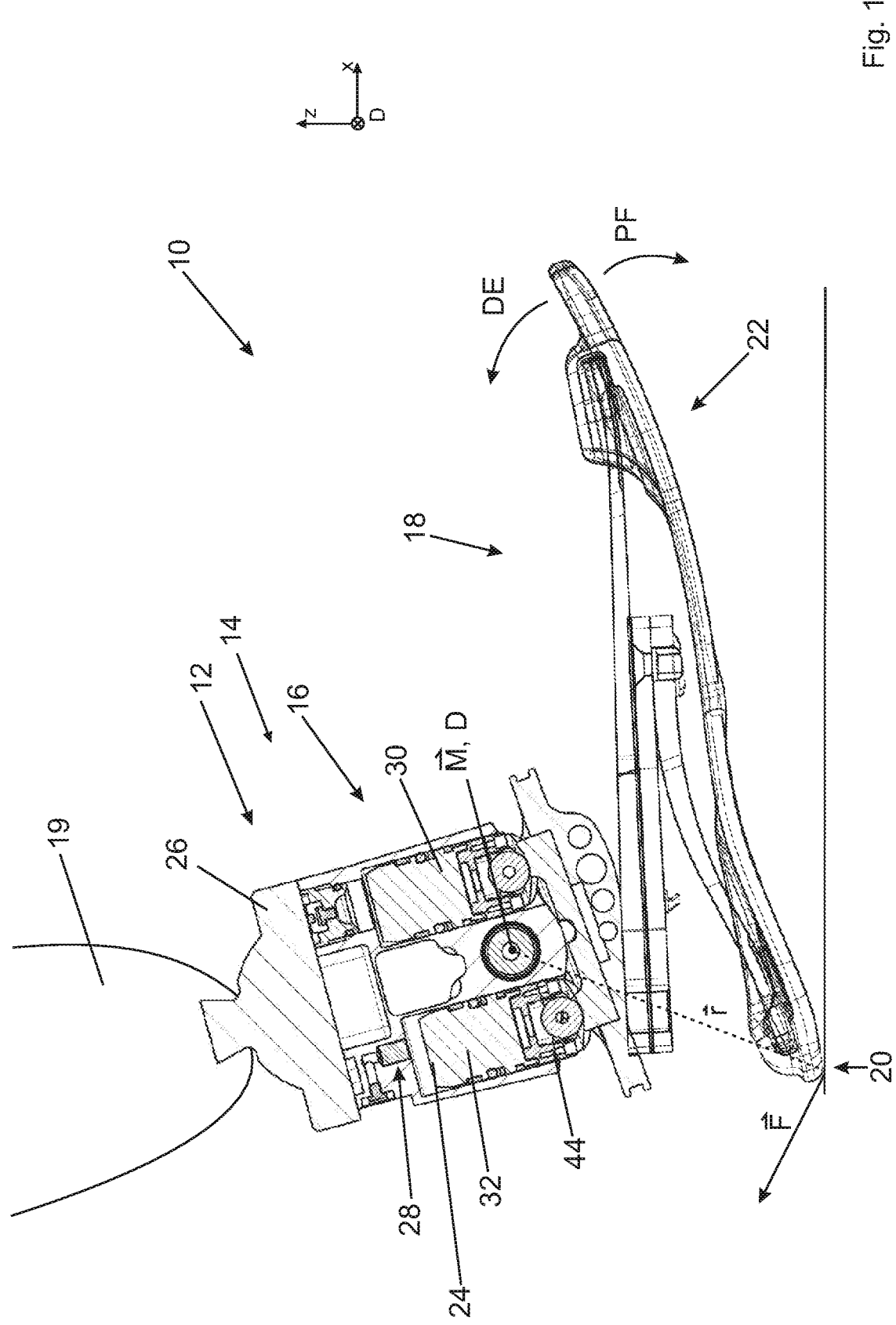

FIG. 1 depicts a foot prosthesis 10 according to the invention, with a lower-leg connection part 12, a release device 16 and a foot part 18. The connecting element 14 acts as a joint so that the foot part 18 can be swivelled relative to the lower-leg connection part 12 in a dorsal extension direction DE, which is indicated by the arrow DE. The foot part 18 can also be swivelled in a plantar flexion direction PF that is opposite to the dorsal extension direction DE. The lower-leg connection part 12 is attached to an artificial lower leg 19.

The foot part 18 comprises a heel section 20 and a ball section 22. The purpose of the release device 16 is to inhibit or facilitate the movement of the foot part 18 relative to the lower-leg connection part 12, depending on the angular position. To achieve this, the release device 16 has a first hydraulic cylinder 24, which is connected to the foot part 18 on the one side by means of a coupling element 26, and to the lower-leg connection part 12 on the other side. The release device 16 also has a hydraulic inhibiting device 28, the outline of which can be identified in FIG. 1 and which is depicted in more detail in FIG. 2a.

The release device 16 also comprises a second hydraulic cylinder 30 that is connected to the first hydraulic cylinder 24 such that a hydraulic fluid 32—in the present case a hydraulic liquid, for example in the form of oil—which is forced out of one of the hydraulic cylinders 24, 30 flows into the other hydraulic cylinder 30, 24.

Figure 2A:
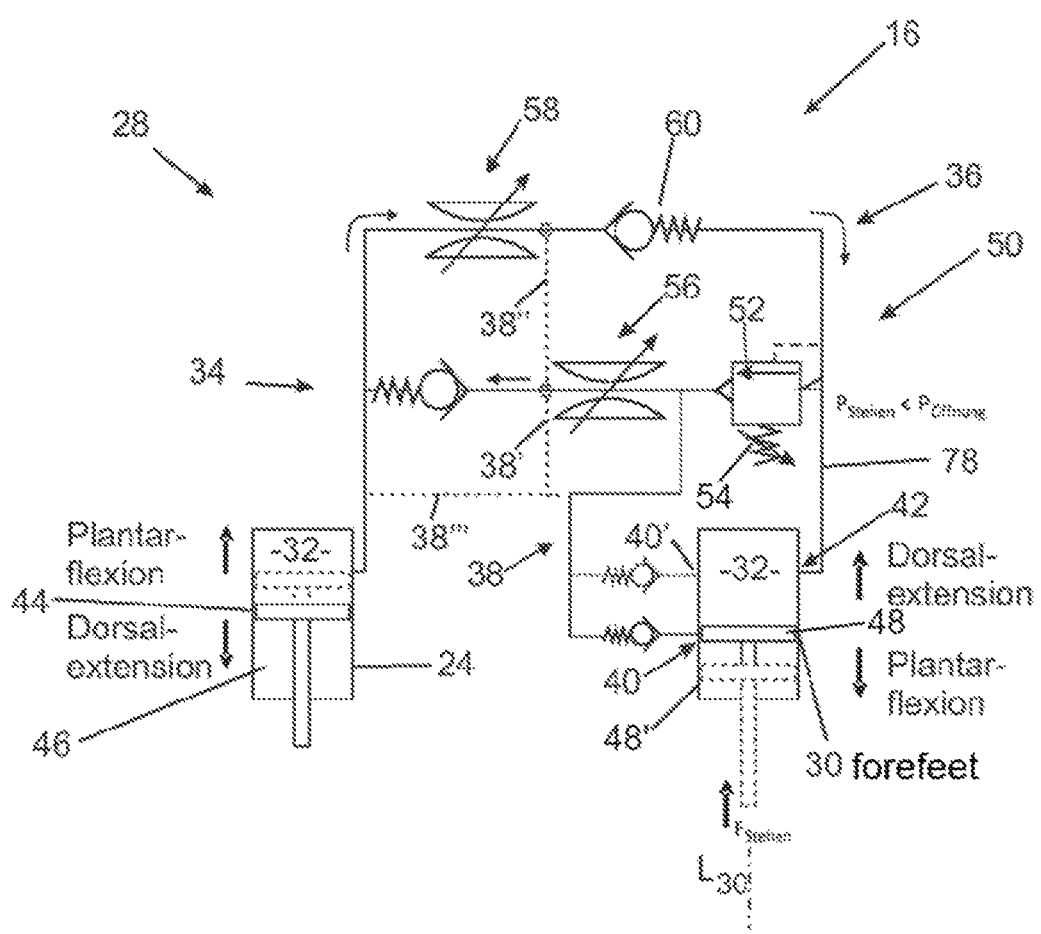

FIG. 2a shows a schematic of the release device 16 with the first hydraulic cylinder 24, the second hydraulic cylinder 30 and the inhibiting device 28, which is composed here of an arrangement of hydraulic elements. The inhibiting device 28 has a first fluid line 34 and a second fluid line 36 which connect the two hydraulic cylinders 24, 30 to one another. The release device 16 also comprises a bypass line 38 that is connected at a tap opening 40 to a cylinder interior 42 of the second hydraulic cylinder 30. The tapping point along a longitudinal axis $L_{32}$ along the second hydraulic cylinder 30 is adjustable, as described below in more detail.

If the foot part 18 (see FIG. 1) executes a dorsal extension motion, a first piston 44 of the first hydraulic cylinder 24 moves in such a way that a cylinder interior 46 expands. A second piston 48 of the second hydraulic cylinder 30 also moves into the cylinder interior 42.

When the foot part 18 (see FIG. 1) is in its zero position in relation to the lower-leg connection part 12, the piston 48 is at the same height as the tap opening 40. This situation is depicted in FIG. 2a. A further dorsal extension motion causes the hydraulic fluid 32 to flow through the first fluid line 34 into the first hydraulic cylinder 24. The hydraulic fluid only passes through the first fluid line 34. This comprises a check valve 50, which has a sequence valve 52 and a non-return valve 54 in the present case. The first fluid line 34 also includes a throttle 56. It is possible, but not necessary, that the throttle 56 is configured to be a separate component. It is also possible that parts of the first fluid line 34 have such a small cross-section that a throttle effect is achieved. According to a preferred embodiment, the throttle 56 is designed to be adjustable so that a flow resistance that the first fluid line sets against the hydraulic fluid can be adjusted.

If the second piston 48 is located in front of the tap opening 40, as indicated by the dashed piston 48', the hydraulic fluid flows through the bypass line 38. It is possible that the bypass line 38 as depicted joins the first fluid line 34 in front of the throttle 56 with regards to a flow direction.

Alternatively, it is possible that the bypass line 38 joins behind the throttle 56 in the direction of flow, which is depicted as the dashed bypass line 38'. The bypass line can also join the second fluid line 36, which is labelled as 38". It is also possible that another throttle is arranged in front of the joining point; this throttle is not depicted. According to another embodiment, the bypass line 38''' discharges directly into the first hydraulic cylinder 24. In this case, it is favourable if the bypass line 38 has its own check valve and, if necessary, its own throttle.

If the foot part 18 executes a plantar flexion motion, the first piston 44 moves into the cylinder interior of the first hydraulic cylinder 24 and the hydraulic fluid only flows through the second fluid line 36 into the second hydraulic cylinder 30. The second fluid line 36 comprises a second throttle 58 and a second check valve 60. It is possible that the bypass line 38 discharges into the second fluid line 36, as depicted by the dot-dash line.

The first check valve 50 has an opening pressure $p_{\textit{Öffnung}}$ and does not open until a pressure $p_{42}$ in the cylinder interior 42 of the second hydraulic cylinder 30 has been exceeded. The opening pressure $p_{\textit{Öffnung}}$ is reached precisely at the point when the projection of the ankle torque $\vec{M}$ on a rotational axis D, about which the foot part 18 swivels relative to the lower-leg connection part 12, exceeds a release threshold value. If a force acts in the ball section 22 that pushes the foot part 18 in the dorsal extension direction DE, this torque is deemed positive. However, if the foot part 18 effects a force that leads to a plantar flexion motion of the foot part, this ankle torque is deemed negative.

Figure 2B:
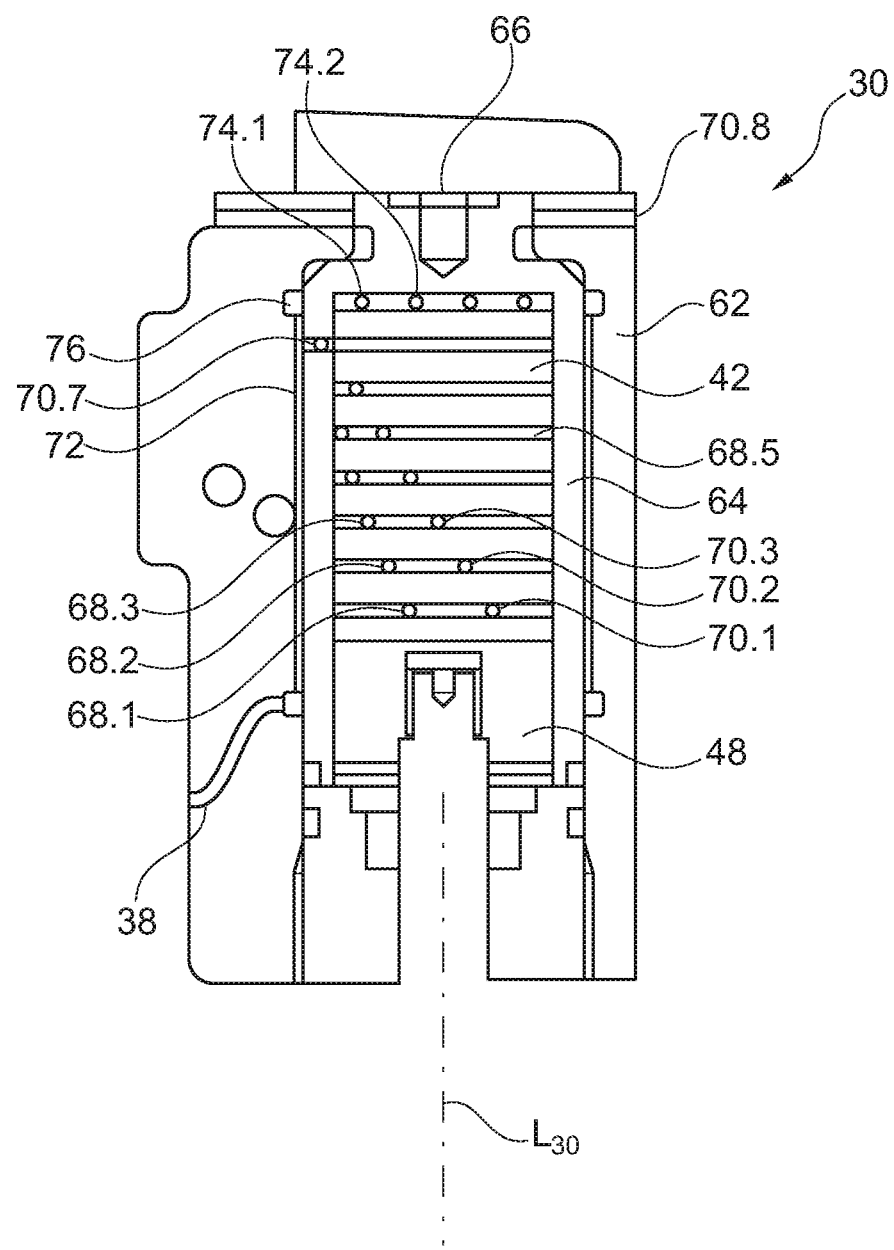

FIG. 2b provides a schematic depiction of the fact that the second hydraulic cylinder 30 has a base body 62, in which a sleeve 64 is arranged such that it can be rotated. The sleeve 64 comprises a coupling structure 66 with which an appropriate tool can engage.

The inner wall of the sleeve 64 forms the interior cylinder wall of the second hydraulic cylinder 30. Several slots 68.1, 68.2, . . . are located in the sleeve 64. The sleeve 64 also has several bores 70.1, 70.2, . . . . In the present case, which represents a preferred embodiment, each slot 68.$i$ ($i$=1, 2, . . . ) has precisely one bore 70.$i$. The bores 70.$i$ are arranged at an angle along the longitudinal axis $L_{30}$. In the present case, the bore 70.7 lies on the sectional plane of the diagram. It should be recognised that the bore 70.7 is connected to a return channel 72. Hydraulic fluid can thus only leave the cylinder interior 42 through the bore 70.7

The sleeve 64 is sealed against the base body 62 and the return channel 72 is arranged around an outer contour of the sleeve 64 in such a way that only one bore, in this case 70.7, is connected to the return channel 72 at all times. In particular, the width of the return channel 72 in the circumferential direction of the sleeve 54 is smaller than the arc length of the angular distance at which the bores 70 are offset from one another. The return channel 72 is part of the bypass line 38.

The slot located at the greatest distance from the piston 48, in the present case the slot 70.8, has several bores 74.1, 74.2, . . . , through which hydraulic fluid can reach an annular channel 76 in every rotational position of the sleeve 64. The annular channel is part of a connecting line 78, which is part of both the first fluid line 34 (see FIG. 2a) and the second fluid line 36.

Figure 3:
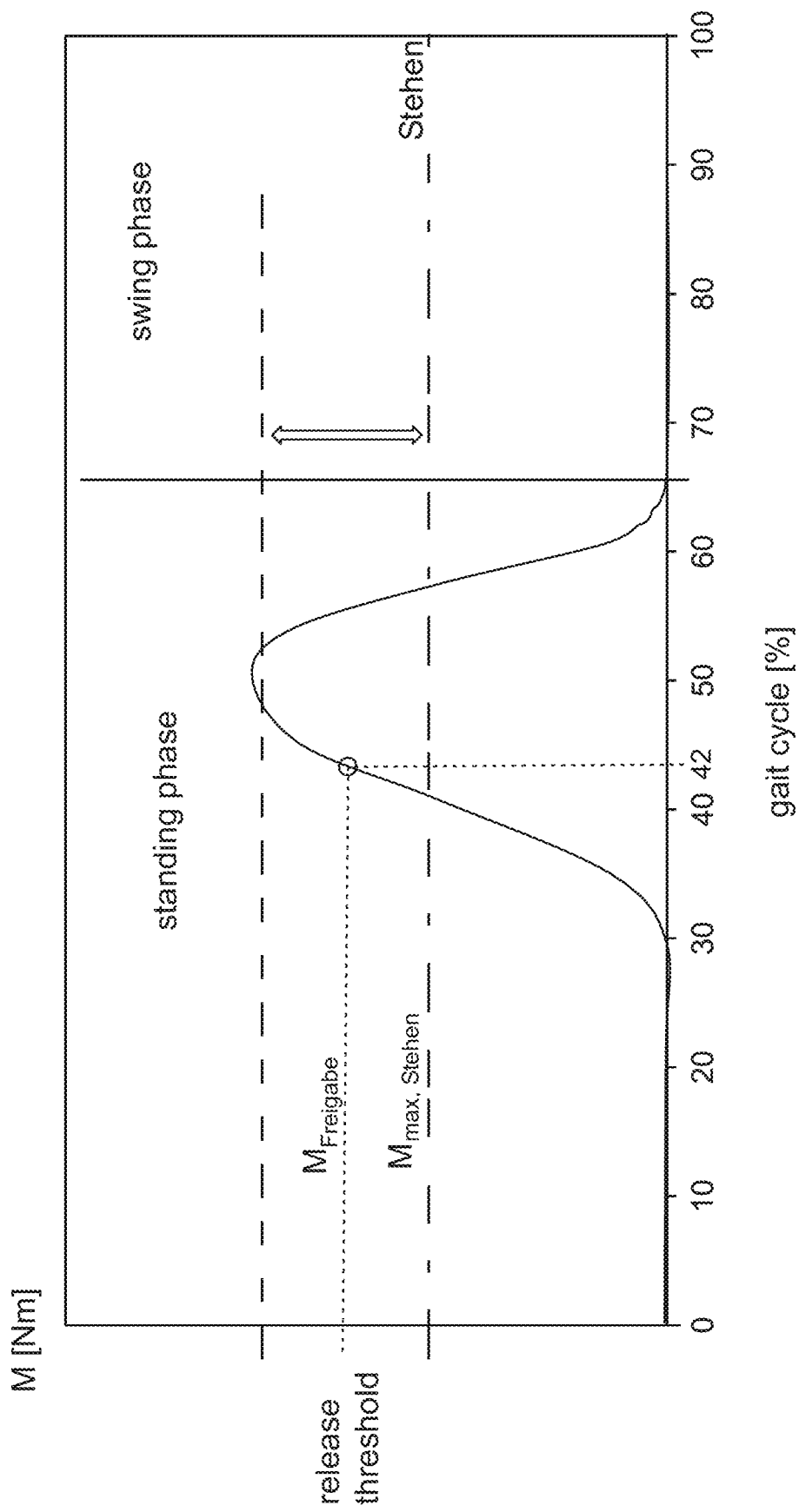

FIG. 3 schematically depicts the progression of the ankle torque M as a scalar quantity of the gait cycle.

It should be recognised that an ankle torque M does not exceed a maximum value $M_{max,Stehen}$ when standing. When walking, however, the ankle torque M exceeds the value $M_{max,Stehen}$. As long as the release threshold value $M_{Freigabe}$ is not exceeded, the release device 16 blocks (see FIG. 1) the movement of the foot part 18.

If the release threshold value $M_{Freigabe}$ is exceeded, the release device 16 releases the dorsal extension motion of the foot part 18. Following the end of the swing phase and the return to the beginning of the gait cycle, the ankle torque M is temporarily negative. This is what happens when the heel section 20 touches the ground. In this case, the release device 16 allows for a plantar flexion motion of the foot part 18 (see FIG. 1).

Figure 4:
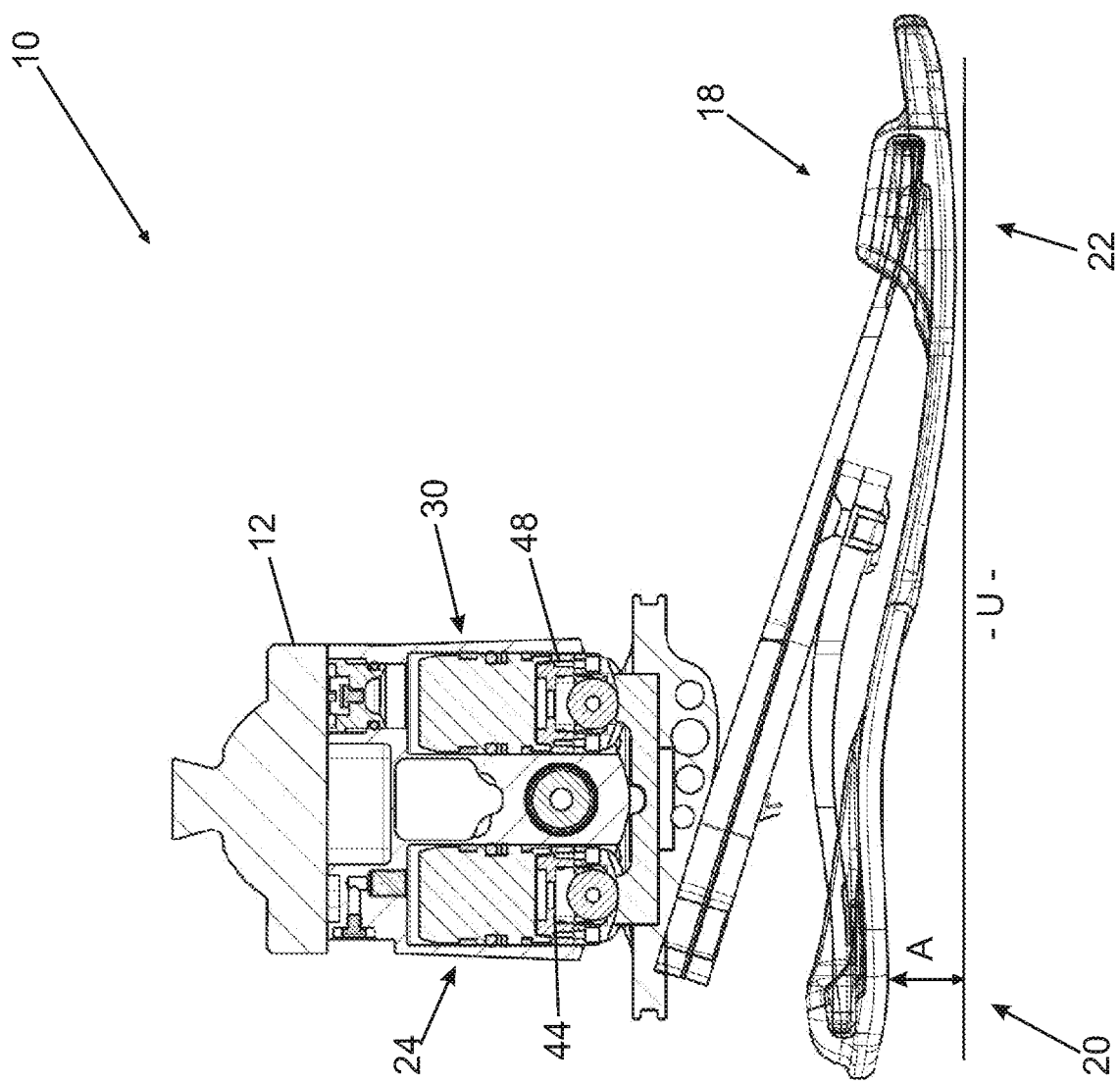

FIG. 4 shows the foot prosthesis 10 with the foot part 18 in its zero position in relation to the lower-leg connection part 12; this may also be described as the neutral position. In this position, the patient is standing. The heel section 20 is located at a heel height A from the ground U. The shoe with the same heel height A is not depicted. In the position shown in FIG. 4, approximately equal forces are acting on the heel section 20 and the ball section 22, the forces being transferred to the ground U via the shoe, which is not depicted. It should be recognised that the pistons 44, 48 of the two hydraulic cylinders 24, 30 are arranged at approximately the same height, which represents a preferred embodiment but is not essential.

Figure 5:
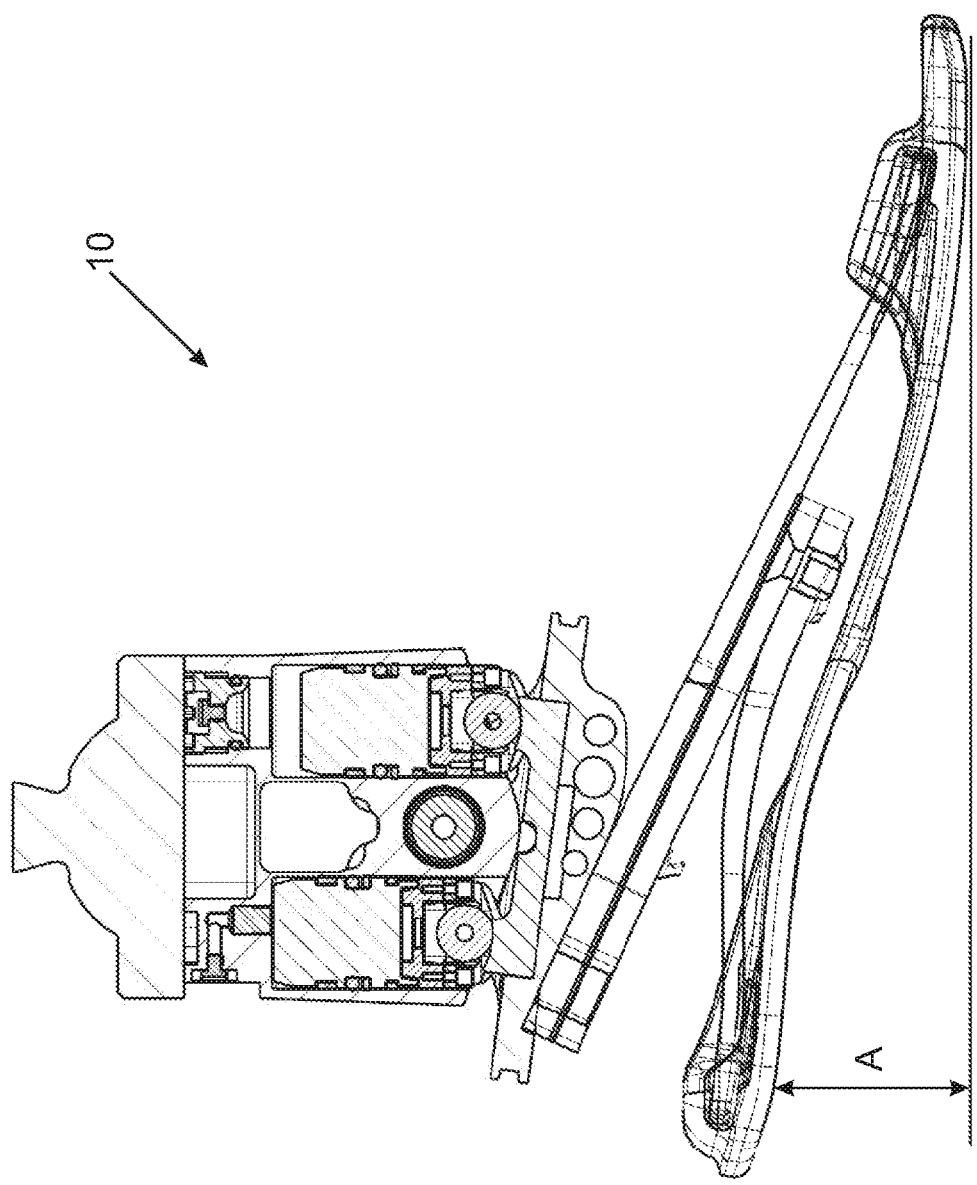

FIG. 5 shows the foot prosthesis 10 in the zero position being used with a shoe with a greater heel height A. In order to create the additional angular offset of the foot part 18 compared to the zero position with a medium heel height, as depicted in FIG. 4, the tap opening 40 is shifted to another tapping point, as described above in FIGS. 2a and 2b. Due to the fact that, with the increased heel height shown in FIG. 5, the maximal ankle torque M is smaller than in the case depicted in FIG. 4, it is advantageous if the opening pressure $p_{\textit{Öffnung}}$ of the check valve 50 is adjustable.

Figure 6:
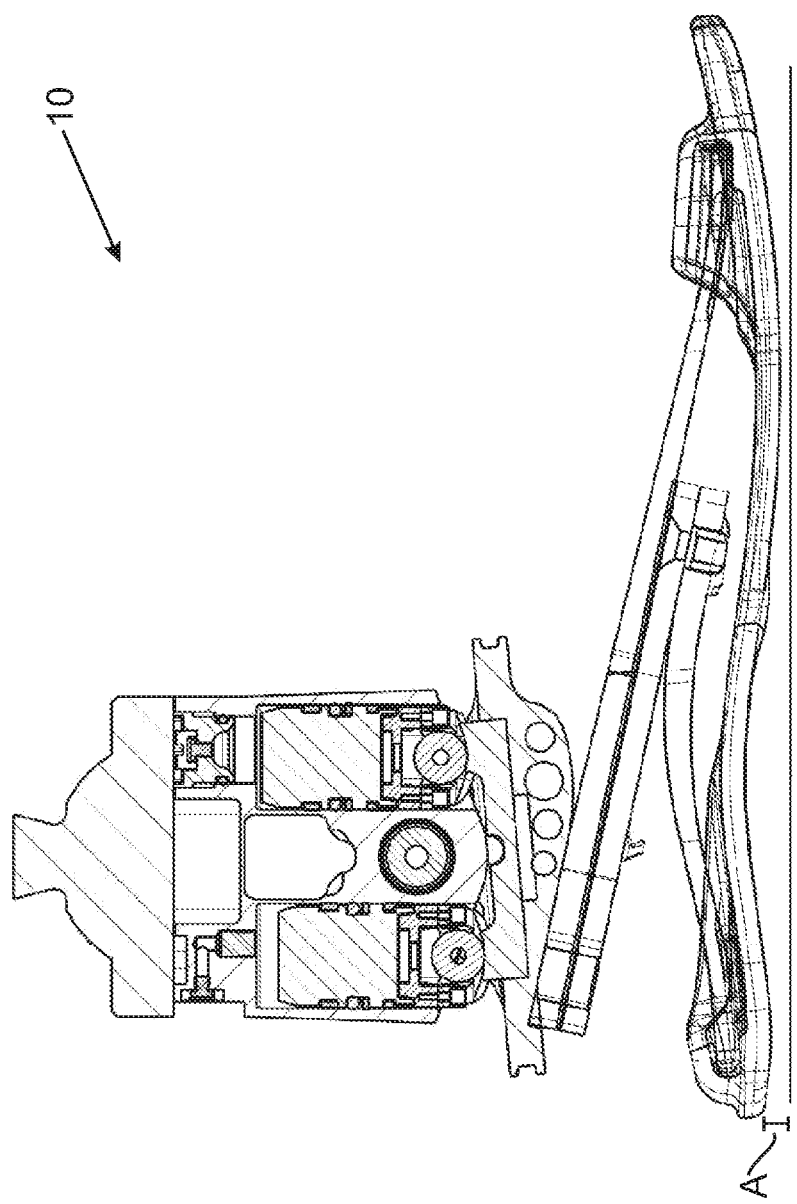

FIG. 6 depicts the foot prosthesis 10 when being used with a shoe with a lower heel height than in FIG. 4. In this case, the angular offset that occurs in comparison to the depiction in FIG. 4 is compensated by adjusting the tapping location of the tap opening 40.

Figure 7:
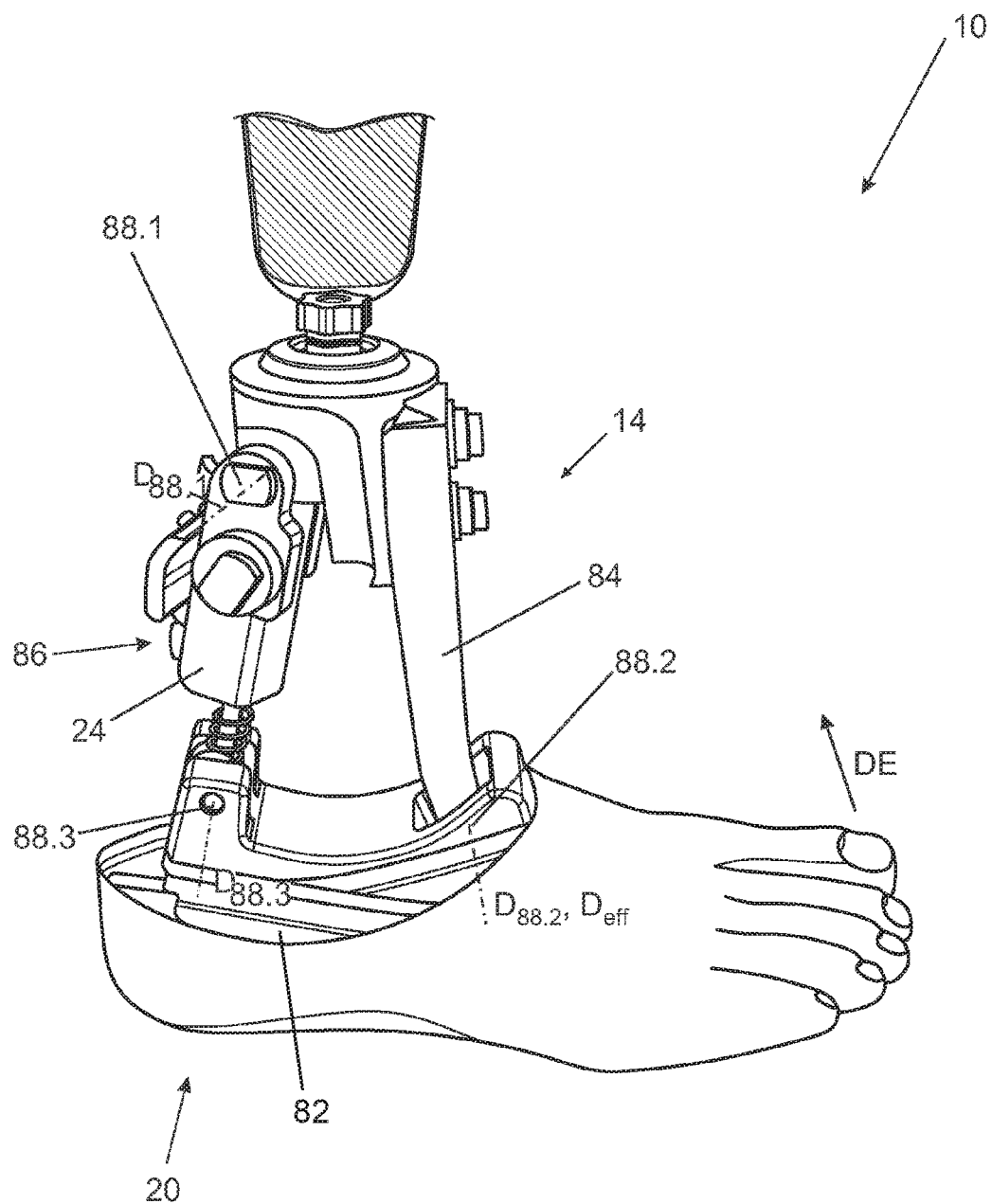

FIG. 7 shows a second embodiment of a foot prosthesis 10 according to the invention. The foot part 18 comprises a foot shell 80 that lends the prosthesis 10 a natural appearance. The foot shell 80 is fixed to a base plate 82, which is also part of the foot part 18. The connecting element 14 comprises a rigid arm 84, which is hinged on the foot part 18. The release device 16 forms a second length-adjustable arm 86, which is connected to the foot part 18 at the heel section 20.

The connecting element 14 has three partial swivel joints 88.1, 88.2, 88.3, which are all swivel joints and each comprise rotational axes $D_{88.1}$, $D_{88.2}$ and $D_{88.3}$. When the prosthesis 10 moves, the foot part 18 rotates relative to the lower-leg connection part 12 about a rotational axis $D_{\textit{eff}}=D_{88.2}$. The hydraulic cylinder 24 is hinged with its piston rod on the partial joint 88.2 and with its cylinder housing on the lower-leg connection part 12.

Figure 8:
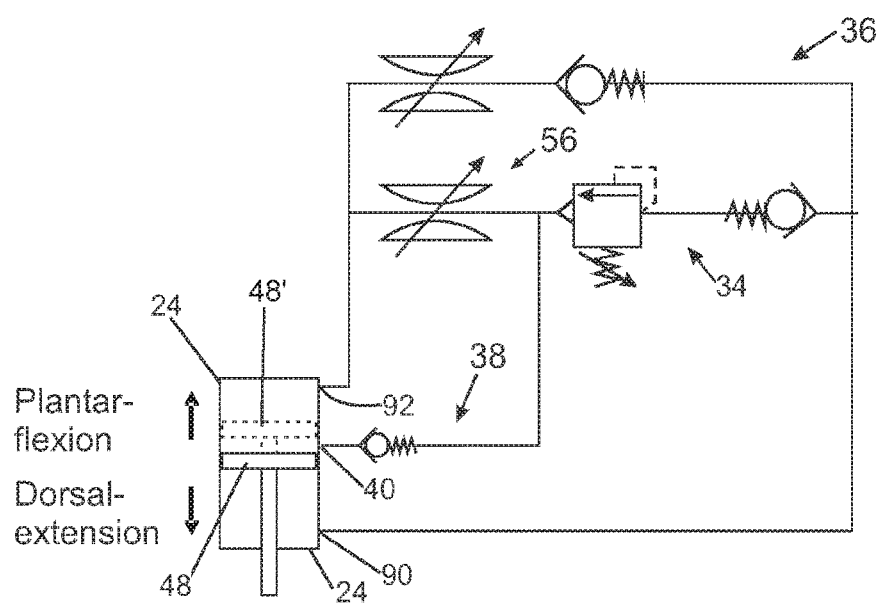

FIG. 8 shows the equivalent hydraulic schematic diagram for the embodiment according to FIG. 7. The hydraulic cylinder 24 is designed to be dual-acting. A dorsal extension motion beyond the zero position, indicated by the piston 48 drawn with a solid line, causes the hydraulic fluid to flow out of an outlet opening 90, through the first fluid line 34 and through an inlet opening 92 back into the hydraulic cylinder 24.

A dorsal extension motion between the maximal plantar flexion position, in which the foot part 18 (see FIG. 7) is arranged in relation to the lower-leg connection part 12 such that its plantar flexion is at its maximum, and the zero position causes the hydraulic fluid to flow through the tap opening 40 and the bypass line 38, as well as through the throttle 56 and the inlet opening 92, back into the hydraulic cylinder 24. A plantar flexion motion causes the hydraulic fluid to flow through the second fluid line 36 and the outlet opening 90 and/or through the bypass line 38.

FIG. 9 shows a foot prosthesis 10 according to the invention according to a further embodiment of the invention. The inhibiting device 28 comprises a sliding element 94 that is tensioned towards an inhibiting structure 98 by a pre-loading element 96. In the present case, the inhibiting structure 98 is configured on the foot part 18. If the sliding element 94 is situated in a first section of the inhibiting structure 98, as depicted by the dashed line and labelled with the reference number 94', it provides only a low resistance to a dorsal extension motion. This low resistance is applied if the foot part 18 is located between a maximal plantar flexion position and the zero position relative to the lower-leg connection part 12. The sliding element 94 also acts as a friction element, meaning that a frictional force must be overcome for the sliding element 94 to move on the inhibiting structure 98.

If the foot part 18 is in its zero position, the sliding element 94 is in a position in which a further movement can only be executed against the spring force of the pre-loading element 96. This is only possible if an ankle torque is acting on the foot part 18 that exceeds the release threshold value. FIG. 9 depicts the foot prosthesis in its maximal dorsal extension position.

The inhibiting device 28 comprises a friction brake 100, by means of which a rotational motion between the foot part 18 and the lower-leg connection part 12 can be braked. In the present case, the friction brake 100 is configured to brake a movement of a pin 102, which is fixed rigidly to the foot part 18, and an intermediate ring 104, which may also be referred to as a coupling ring. The intermediate ring 104 is designed such that it can be rotated relative to both the foot part 18 and the lower-leg connection part 12.

The release device 16 comprises a mechanical return element 106, which is connected to the foot part 18 in such a way that a dorsal extension motion of the foot part 18 does not cause a relative movement between the foot part 18 and the intermediate ring 104. Conversely, the return element 106 enables a movement between the intermediate ring 104 and the foot part 18 if the foot part 18 executes a plantar flexion motion. This means that the friction brake 100 can only brake a dorsal extension motion of the foot part, but not a plantar flexion motion. The release threshold value $M_{Freigabe}$ can be adjusted by pre-loading the spring 96.

It is possible and represents a preferred embodiment for the inhibiting structure 98 to be fixed in relation to the foot part 18 such that it can be detached in a radial direction relative to the rotational axis D. For example, the inhibiting structure 98 is designed to be situated on a moveable adjustment part, which can be set in relation to the foot part 18. In this case, this adjustment part can first of all be detached from the foot part 18, then swivelled relative to the foot part 18 about the rotational axis D, and then re-attached to the foot part 18. This results in a change in the angular position, in which the foot part 18 is in the zero position. The zero position from which the dorsal extension motion is more intensely inhibited can thus be set.

| Reference list | |
|---|---|
| 10 | foot prosthesis |
| 12 | lower-leg connection part |
| 14 | connecting element |

Reference list

| | |
|---|---|
| 16 | release device |
| 18 | foot part |
| 19 | lower leg |
| 20 | heel section |
| 22 | ball section |
| 24 | hydraulic cylinder |
| 26 | coupling element |
| 28 | inhibiting device |
| 30 | second hydraulic cylinder |
| 32 | hydraulic fluid |
| 34 | first fluid line |
| 36 | second fluid line |
| 38 | bypass line |
| 40 | tap opening |
| 42 | cylinder interior |
| 44 | first piston |
| 46 | cylinder interior |
| 48 | second piston |
| 50 | check valve |
| 52 | sequence valve |
| 54 | non-return valve |
| 56 | throttle |
| 58 | second throttle |
| 60 | second check valve |
| 62 | base body |
| 64 | sleeve |
| 66 | coupling structure |
| 68 | groove |
| 70 | bore |
| 72 | return channel |
| 74 | bore |
| 76 | annular channel |
| 78 | connecting line |
| 80 | foot shell |
| 82 | base plate |
| 84 | rigid arm |
| 86 | partial swivel joint |
| 90 | discharge opening |
| 92 | inlet opening |
| 94 | sliding element |
| 96 | pre-loading element |
| 98 | inhibiting structure |
| 100 | friction brake |
| 102 | pin |
| 104 | intermediate ring |
| 106 | return element |
| A | heel height |
| D | rotational axis |
| DE | dorsal extension direction |
| $L_{30}$ | longitudinal axis |
| $M_{Freigabe}$ | release threshold value |
| M | Ankle torque |
| $P_{öffnung}$ | opening pressure |
| PF | plantar flexion direction |
| U | ground |

The invention claimed is:

1. A foot prosthesis, comprising:
a lower-leg connection part;
a foot part;
a connecting element with a joint that connects the lower-leg connection part with the foot part;
a release device operable to inhibit and disinhibit a motion of the foot part relative to the lower-leg connection part, the release device comprising a passive inhibiting device that is designed in such a way that a dorsal extension motion of the foot part in relation to the lower-leg connection part in an angular range from a maximal plantar flexion position to a zero position is inhibited less intensely than a dorsal extension motion of the foot part from the zero position;
wherein the release device is designed in such a way that it only releases the dorsal extension motion of the foot part beyond the zero position if an ankle torque acting on the foot part lies above a predetermined release threshold value.

2. The foot prosthesis according to claim 1, wherein the release device is designed in such a way that the zero position can be adjusted.

3. The foot prosthesis according to claim 1, wherein
the release device has a hydraulic cylinder that is connected to the foot part and the lower-leg connection part, and
the inhibiting device is a hydraulic device that is connected in fluid communication with the hydraulic cylinder such that a dorsal extension motion of the foot part in relation to the lower-leg connection part in an angular range from a maximal plantar flexion position to a zero position is inhibited less intensely than a dorsal extension motion of the foot part from the zero position.

4. The foot prosthesis according claim 3, wherein the inhibiting device comprises:
a first fluid line through which the hydraulic fluid flows when the foot part executes a dorsal extension motion beyond the zero position, the first fluid line having a first flow resistance;
a bypass line through which the hydraulic fluid flows when the foot part executes a dorsal extension motion between the maximal plantar flexion position and the zero position,
the bypass line having a bypass flow resistance that is smaller than the first flow resistance.

5. The foot prosthesis according to claim 4, wherein the first fluid line comprises a check valve, the check valve arranged to:
prevent a dorsal extension motion beyond the zero position, provided that an ankle torque acting on the foot part does not lie above a release threshold value, and
release a dorsal extension motion beyond the zero position if the ankle torque lies above the release threshold value.

6. The foot prosthesis according to claim 4, wherein the inhibiting device has a second fluid line through which the hydraulic fluid flows when the foot part executes a plantar flexion motion, and the second fluid line has a second flow resistance that is smaller than the first flow resistance.

7. The foot prosthesis according to claim 4, wherein the release device comprises a second hydraulic cylinder, which is connected to the inhibiting device in such a way that:
a dorsal extension motion beyond the zero position causes the hydraulic fluid to flow out of the second hydraulic cylinder, through the first fluid line, and into the first hydraulic cylinder;
a dorsal extension motion between the maximal plantar flexion position and the zero position causes the hydraulic fluid to flow out of the second hydraulic cylinder, through the bypass line, and into the first hydraulic cylinder;
a plantar flexion motion causes the hydraulic fluid to flow out of the second hydraulic cylinder, through the first fluid line, and into the first hydraulic cylinder.

8. The foot prosthesis according to claim 7, wherein the bypass line is connected to the first hydraulic cylinder or the second hydraulic cylinder such that a tapping point of a tap opening along a longitudinal axis of the hydraulic cylinder can be changed to set the zero position.

9. The foot prosthesis according to claim 4, wherein the hydraulic cylinder is configured to be dual-acting and is connected to the inhibiting device in such a way that:

a dorsal extension motion beyond the zero position causes the hydraulic fluid to flow out of an outlet opening, which is arranged at an outlet end of the hydraulic cylinder, through the first fluid line and back into the first hydraulic cylinder;

a dorsal extension motion between the maximal plantar flexion position and the zero position causes the hydraulic fluid to flow through a tap opening and the bypass line;

a plantar flexion motion causes the hydraulic fluid to flow through a second fluid line or the bypass line.

10. The foot prosthesis according to claim 3, wherein the cylinder is a linear cylinder.

11. The foot prosthesis according to claim 1, wherein the release device comprises:
    a friction brake;
    a mechanical return element arranged such that a dorsal extension motion of the foot part is braked more intensely than a plantar flexion motion.

12. A foot prosthesis, comprising:
    a lower-leg connection part;
    a foot part;
    a connecting element that connects the lower-leg connection part with the foot part;
    a release device to control movement of the foot part relative to the lower-leg connection part, the release device having a passive inhibiting device to inhibit a dorsal extension motion of the foot part relative to the lower-leg connection part in an angular range from a maximal plantar flexion position to a zero position less intensely than a dorsal extension motion of the foot part from the zero position, and the release device releases the dorsal extension motion of the foot part beyond the zero position only if an ankle torque acting on the foot part is above a predetermined release threshold value.

13. The foot prosthesis according to claim 12, wherein the release device has an adjustable zero position.

14. The foot prosthesis according to claim 12, wherein the release device has a hydraulic cylinder that is connected to the foot part and the lower-leg connection part, and the inhibiting device is a hydraulic device that is connected in fluid communication with the hydraulic cylinder to inhibit a dorsal extension motion of the foot part in relation to the lower-leg connection part in an angular range from a maximal plantar flexion position to a zero position less intensely than a dorsal extension motion of the foot part from the zero position.

15. The foot prosthesis according claim 14, wherein the inhibiting device comprises:
    a first fluid line through which the hydraulic fluid flows when the foot part executes a dorsal extension motion beyond the zero position, the first fluid line having a first flow resistance;
    a bypass line through which the hydraulic fluid flows when the foot part executes a dorsal extension motion between the maximal plantar flexion position and the zero position, the bypass line having a bypass flow resistance that is smaller than the first flow resistance.

16. The foot prosthesis according to claim 15, wherein the first fluid line comprises a check valve, the check valve to prevent a dorsal extension motion beyond the zero position, provided that an ankle torque acting on the foot part does not lie above a release threshold value, and release a dorsal extension motion beyond the zero position if the ankle torque lies above the release threshold value.

17. The foot prosthesis according to claim 15, wherein the inhibiting device has a second fluid line through which the hydraulic fluid flows when the foot part executes a plantar flexion motion, and the second fluid line has a second flow resistance that is smaller than the first flow resistance.

18. The foot prosthesis according to claim 15, wherein the release device comprises a second hydraulic cylinder, which is connected to the inhibiting device in such a way that:
    a dorsal extension motion beyond the zero position causes the hydraulic fluid to flow out of the second hydraulic cylinder, through the first fluid line, and into the first hydraulic cylinder;
    a dorsal extension motion between the maximal plantar flexion position and the zero position causes the hydraulic fluid to flow out of the second hydraulic cylinder, through the bypass line, and into the first hydraulic cylinder;
    a plantar flexion motion causes the hydraulic fluid to flow out of the second hydraulic cylinder, through the first fluid line, and into the first hydraulic cylinder.

19. The foot prosthesis according to claim 15, wherein the hydraulic cylinder is configured to be dual-acting and is connected to the inhibiting device in such a way that:
    a dorsal extension motion beyond the zero position causes the hydraulic fluid to flow out of an outlet opening, which is arranged at an outlet end of the hydraulic cylinder, through the first fluid line, and back into the first hydraulic cylinder;
    a dorsal extension motion between the maximal plantar flexion position and the zero position causes the hydraulic fluid to flow through a tap opening and the bypass line;
    a plantar flexion motion causes the hydraulic fluid to flow through a second fluid line or the bypass line.

20. A foot prosthesis, comprising:
    a lower-leg connection part;
    a foot part;
    a connecting element with a joint that connects the lower-leg connection part with the foot part;
    a release device operable to inhibit and disinhibit a motion of the foot part relative to the lower-leg connection part,
    the release device comprising a passive inhibiting device that is designed in such a way that a dorsal extension motion of the foot part in relation to the lower-leg connection part in an angular range from a maximal plantar flexion position to a zero position is inhibited less intensely than a dorsal extension motion of the foot part from the zero position;
    the release device has a hydraulic cylinder that is connected to the foot part and the lower-leg connection part, and the inhibiting device is connected to the hydraulic cylinder such that a dorsal extension motion of the foot part in relation to the lower-leg connection part in an angular range from a maximal plantar flexion position to a zero position is inhibited less intensely than a dorsal extension motion of the foot part from the zero position;
    the inhibiting device comprises:
        a first fluid line through which the hydraulic fluid flows when the foot part executes a dorsal extension motion beyond the zero position, the first fluid line having a first flow resistance;
        a bypass line through which the hydraulic fluid flows when the foot part executes a dorsal extension motion between the maximal plantar flexion position and the zero position,
        the bypass line having a bypass flow resistance that is smaller than the first flow resistance.

21. The foot prosthesis according to claim 20, wherein the first fluid line comprises a check valve, the check valve arranged to:
prevent a dorsal extension motion beyond the zero position, provided that an ankle torque acting on the foot part does not lie above a release threshold value, and
release a dorsal extension motion beyond the zero position if the ankle torque lies above the release threshold value.

22. The foot prosthesis according to claim 20, wherein the inhibiting device has a second fluid line through which the hydraulic fluid flows when the foot part executes a plantar flexion motion, and the second fluid line has a second flow resistance that is smaller than the first flow resistance.

23. The foot prosthesis according to claim 20, wherein the release device comprises a second hydraulic cylinder, which is connected to the inhibiting device in such a way that:
a dorsal extension motion beyond the zero position causes the hydraulic fluid to flow out of the second hydraulic cylinder, through the first fluid line, and into the first hydraulic cylinder;
a dorsal extension motion between the maximal plantar flexion position and the zero position causes the hydraulic fluid to flow out of the second hydraulic cylinder, through the bypass line, and into the first hydraulic cylinder;
a plantar flexion motion causes the hydraulic fluid to flow out of the second hydraulic cylinder, through the first fluid line, and into the first hydraulic cylinder.

24. The foot prosthesis according to claim 23, wherein the bypass line is connected to the first hydraulic cylinder or the second hydraulic cylinder such that a tapping point of a tap opening along a longitudinal axis of the hydraulic cylinder can be changed to set the zero position.

25. A foot prosthesis, comprising:
a lower-leg connection part;
a foot part;
a connecting element that connects the lower-leg connection part with the foot part;
a release device to control movement of the foot part relative to the lower-leg connection part, the release device having a passive inhibiting device to inhibit a dorsal extension motion of the foot part relative to the lower-leg connection part in an angular range from a maximal plantar flexion position to a zero position less intensely than a dorsal extension motion of the foot part from the zero position;
wherein the release device has a hydraulic cylinder that is connected to the foot part and the lower-leg connection part, and the inhibiting device is connected to the hydraulic cylinder to inhibit a dorsal extension motion of the foot part in relation to the lower-leg connection part in an angular range from a maximal plantar flexion position to a zero position less intensely than a dorsal extension motion of the foot part from the zero position;
wherein the inhibiting device comprises:
a first fluid line through which the hydraulic fluid flows when the foot part executes a dorsal extension motion beyond the zero position, the first fluid line having a first flow resistance;
a bypass line through which the hydraulic fluid flows when the foot part executes a dorsal extension motion between the maximal plantar flexion position and the zero position, the bypass line having a bypass flow resistance that is smaller than the first flow resistance.

26. The foot prosthesis according to claim 25, wherein the first fluid line comprises a check valve, the check valve to prevent a dorsal extension motion beyond the zero position, provided that an ankle torque acting on the foot part does not lie above a release threshold value, and release a dorsal extension motion beyond the zero position if the ankle torque lies above the release threshold value.

27. The foot prosthesis according to claim 25, wherein the inhibiting device has a second fluid line through which the hydraulic fluid flows when the foot part executes a plantar flexion motion, and the second fluid line has a second flow resistance that is smaller than the first flow resistance.

28. The foot prosthesis according to claim 25, wherein the release device comprises a second hydraulic cylinder, which is connected to the inhibiting device in such a way that:
a dorsal extension motion beyond the zero position causes the hydraulic fluid to flow out of the second hydraulic cylinder, through the first fluid line, and into the first hydraulic cylinder;
a dorsal extension motion between the maximal plantar flexion position and the zero position causes the hydraulic fluid to flow out of the second hydraulic cylinder, through the bypass line, and into the first hydraulic cylinder;
a plantar flexion motion causes the hydraulic fluid to flow out of the second hydraulic cylinder, through the first fluid line, and into the first hydraulic cylinder.

* * * * *